United States Patent [19]

Saville

[11] Patent Number: Plant 6,213

[45] Date of Patent: Jul. 5, 1988

[54] ROSE PLANT

[75] Inventor: F. Harmon Saville, Rowley, Mass.

[73] Assignee: Nor'East Miniature Roses, Inc., Rowley, Mass.

[21] Appl. No.: 884,755

[22] Filed: Jul. 11, 1986

[51] Int. Cl.[4] ..... A01H 5/00

[52] U.S. Cl. ..... Plt./8

[58] Field of Search ..... Plt. 8

*Primary Examiner*—Robert E. Bagwill

*Attorney, Agent, or Firm*—Vincent G. Gioia

[57] ABSTRACT

A new miniature rose variety of attractive Chinese yellow coloring that maintains color well through development and aging.

1 Drawing Sheet

1

The present invention relates to a new and distinct variety of rose plant of the miniature rose class, which was originated by my crossing as seed parent the rose known as "Golden Slippers" (U.S. Plant Pat. No. 2,244) and as pollen parent the rose known as "Rise 'N Shine" (U.S. Plant Pat. No. 4,231). The varietal denomination of this new variety is "Savasun".

Among the novel characteristics possessed by this new variety which distinguish it from its parents and all other varieties of which I am aware are its attractive Chinese yellow colored flowers that maintain their color and form through development and aging. Asexual reproduction by budding of the new variety as performed in Essex County, Mass., shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.). The terminology used in color description herein refers to plate numbers in the aforementioned color chart, e.g., "16B" is plate 16B of The Royal Horticultural Society Colour Chart.

Parentage: Seedling.

*Seed parent.*—"Golden Slippers".

*Pollen parent.*—"Rise 'N Shine".

Class: Miniature.

The following observations are made of specimens grown under glass in Essex County, Mass., during the month of March.

FLOWER

Blooming habit: Recurrent.

A. Bud:

(1) *Size.*—Medium.

(2) *Form.*—Long, pointed.

(3) *Color.*—As sepals divide, color is near Chinese yellow, e.g., 16B, 20B.

(4) *Sepals.*—Longer than bud, lightly foliated.

(5) *Peduncle.*—Length — about 1 inch. Aspect — straight. Strength — erect. Color — near 143C.

B. Bloom:

2

(1) *Size.*—Average size when fully expanded — about 1⅝ inches.

(2) *Borne.*—Primarily singly.

(3) *Form.*—High centered at first, becoming flat, petals reflex to points and roll under upon opening but retain pointed apices. Flower tends to be globular.

(4) *Petalage.*—Number of petals under normal conditions — about 28–30.

(5) *Color.*—As petals unfurl to ½ open stage, Chinese yellow coloring remains relatively constant appearing as 16A through 16C. At flower center, where petals bunch, deeper tonality, 20A, is predominant. Outer petals lighten slightly to near 18B to C upon aging and increased exposure to light. Petals exhibit veining with near white highlights.

C. Petals:

(1) *Texture.*—Average.

(2) *Appearance.*—Inside — satiny, outside — satiny.

(3) *Form.*—Broad, fan shaped with pronounced apex on many petals.

(4) *Arrangement.*—Regularly arranged, imbricated.

(5) *Petaloids in center.*—Few.

(6) *Persistence.*—Drop off cleanly.

(7) *Fragrance.*—None.

(8) *Lasting quality.*—Average on plant and as cut flower.

REPRODUCTIVE ORGANS

A. Stamens, filaments and anthers:

(1) *Arrangement.*—Regularly arranged around styles.

(2) *Color.*—Near 21A.

B. Pollen:

*Color.*—Near 17A.

C. Styles: Medium length, thin.

D. Stigmas:

*Color.*—Near 5D.

E. Hips: None observed.

PLANT

A. Form: Upright, compact.

B. Growth: Very vigorous, uniform branching.

*Height attained.*—About 14 to 16 inches.

C. Foliage: Compound 5 to 7 leaflets.

(1) *Size.*—Medium.

(2) *Quantity.*—Abundant.

(3) *Color.*—New foliage: Upper side — near to 138A. Under side — near to 143A. Old foliage:

Upper side — near 139A. Under side — near 137A.

(4) *Shape.*—Oval, pointed.

(5) *Texture.*—Upper side is glossy and under side is matte.

(6) *Edge.*—Serrated.

(7) *Serration.*—Serrate.

(8) *Leaf stem.*—Color — near 147B. Under side — near 147C.

(9) *Stipules.*—Medium, slightly bearded.

(10) *Resistance to disease.*—Blackspot — average. Mildew — average. Rust — average.

D. Wood:

(1) *New wood.*—Color — near 148B. Bark — smooth.

(2) *Old wood.*—Color — near 138A. Bark — smooth.

E. Thorns:

(1) *Thorns.*—Quantity (main stalk) — ordinary. On laterals from stalk — few. Form — long, thin, straight, pointed. Length — medium. Color — near 183B. Position — irregular.

(2) *Prickles.*—None.

F. Winter hardiness: Requires ordinary protection in extreme climates.

I claim:

1. A new and distinct variety of rose plant of the miniature rose class, substantially as shown and described, characterized particularly by attractive Chinese yellow colored flowers that hold color well through development and aging.

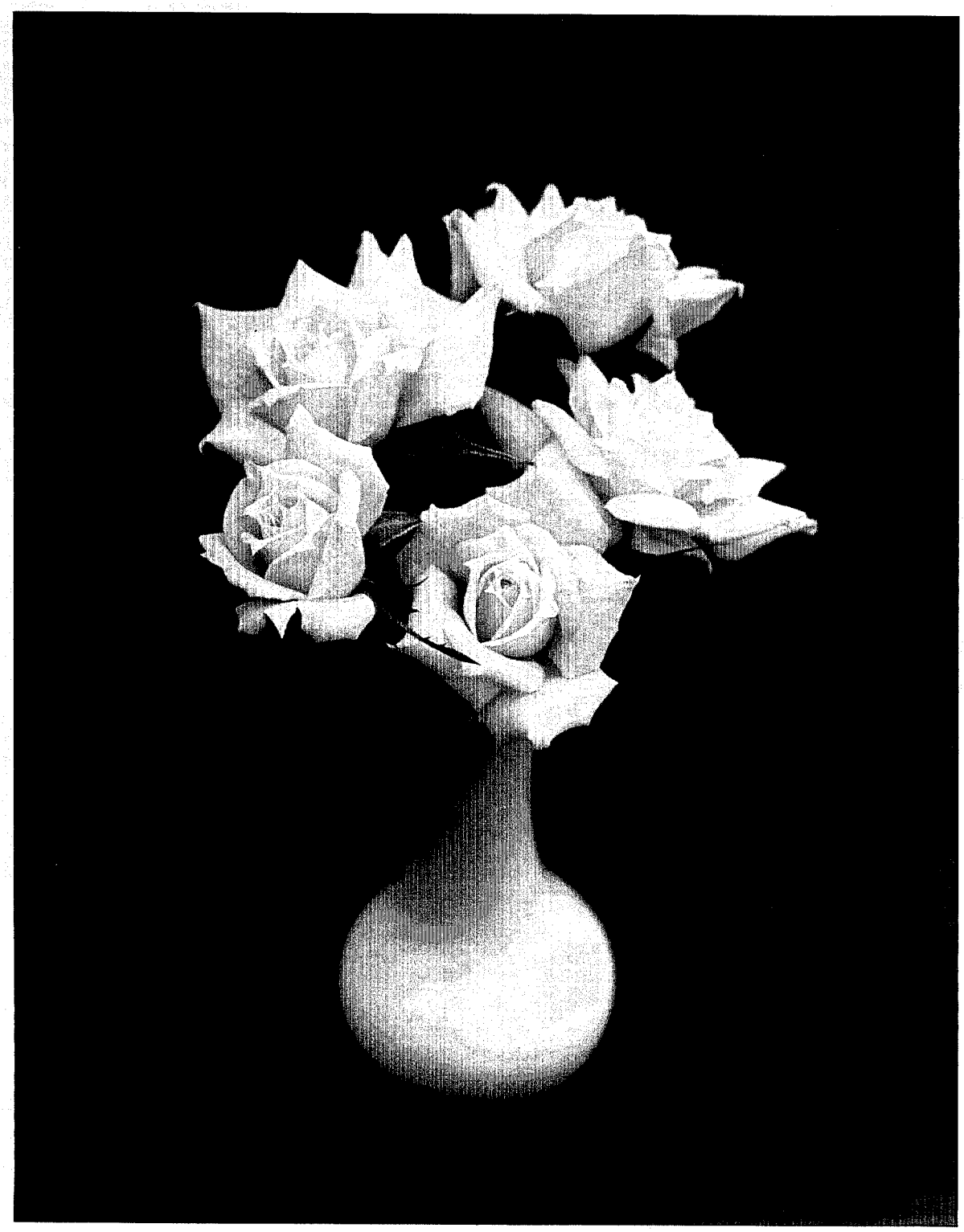

* * * * *